(12) United States Patent
Mondloch et al.

(10) Patent No.: US 8,025,424 B2
(45) Date of Patent: Sep. 27, 2011

(54) LED LIGHTING SYSTEM FOR USE IN ENVIRONMENTS WITH HIGH MAGNETIC FIELDS OR THAT REQUIRE LOW EMI EMISSIONS

(75) Inventors: Michael J. Mondloch, Waukesha, WI (US); Harry M. Pyne, New Berlin, WI (US); David A. Venhaus, West Allis, WI (US)

(73) Assignee: Everbrite, LLC, Greenfield, WI (US)

( * ) Notice: Subject to any disclaimer, the term of this patent is extended or adjusted under 35 U.S.C. 154(b) by 0 days.

(21) Appl. No.: 12/629,270

(22) Filed: Dec. 2, 2009

(65) Prior Publication Data

US 2010/0181916 A1    Jul. 22, 2010

Related U.S. Application Data

(63) Continuation of application No. 11/604,118, filed on Nov. 24, 2006, now Pat. No. 7,629,570.

(60) Provisional application No. 60/739,638, filed on Nov. 26, 2005.

(51) Int. Cl.
*G01J 1/04* (2006.01)
(52) U.S. Cl. .................................. 362/249.02; 362/294
(58) Field of Classification Search ............. 362/249.02, 362/249.11, 294, 373, 800
See application file for complete search history.

(56) References Cited

U.S. PATENT DOCUMENTS

| | | | |
|---|---|---|---|
| 6,354,714 B1 | 3/2002 | Rhodes | |
| 6,367,949 B1 | 4/2002 | Pederson | |
| 6,371,637 B1 | 4/2002 | Atchinson et al. | |
| 6,600,274 B1 | 7/2003 | Hughes | |
| 6,609,804 B2 | 8/2003 | Nolan et al. | |
| 6,786,625 B2 | 9/2004 | Wesson | |
| 6,789,930 B2 * | 9/2004 | Pederson | 362/545 |
| 6,860,628 B2 | 3/2005 | Robertson et al. | |
| 6,871,981 B2 | 3/2005 | Alexanderson et al. | |
| 6,880,952 B2 | 4/2005 | Kiraly et al. | |
| 7,157,866 B2 * | 1/2007 | Komiya et al. | 315/312 |
| 7,511,259 B2 | 3/2009 | Nyffenegger et al. | |

* cited by examiner

*Primary Examiner* — Anabel Ton
(74) *Attorney, Agent, or Firm* — Michael Best & Friedrich LLP

(57) ABSTRACT

Lighting fixtures and lighting systems for use in areas with high magnetic fields or areas that require low EMI emissions. The lighting systems include a non-ferrous lighting fixture having an LED light source and a control circuit. The LED light source includes one or more LEDs, and the control circuit provides a regulated operational current to the LED light source. The control circuit includes at least one switch for controlling the flow of current through the control circuit. The switch has a first state and a second state, and the operational current provided to the LED light source is increased and decreased in a linear manner based on the state of the at least one switch.

20 Claims, 8 Drawing Sheets

LED LIGHTING SYSTEM FOR USE IN ENVIRONMENTS WITH HIGH MAGNETIC FIELDS OR THAT REQUIRE LOW EMI EMISSIONS

RELATED APPLICATIONS

This application is a continuation of U.S. patent application Ser. No. 11/604,118, filed Nov. 24, 2006, which claims the benefit of U.S. Provisional Patent Application Ser. No. 60/739,638, filed Nov. 26, 2005, the entire contents of both of which are hereby incorporated by reference.

FIELD OF THE INVENTION

This invention relates to lighting systems, specifically it is a light emitting diode (LED) lighting system that is designed entirely of non-ferrous materials and employs low RF noise driver electronics for use with high magnetic field/low electromagnetic interference (EMI) environments, such as magnetic resonance imagery (MRI) equipment applications.

DISCUSSION OF RELATIVE ART

MRI technology utilizes extremely strong magnetic fields in the order of 0.5 to over 7 Tesla. In addition, the nature of MRI signal acquisition requires a very low radio frequency (RF) noise environment to preserve image quality. These strong magnetic fields and low noise requirements pose substantial difficulties for equipment operating in the vicinity of a MRI scanner. In the past, when lighting an area that surrounds MRI equipment, facility designers had several options, including fluorescent lighting, incandescent lighting, and metal halide lighting, all of which contained ferrous metals, or materials made from iron. These designers soon discovered two (2) issues associated with the use of ferrous materials to light an area that surrounds MRI equipment.

First, ferrous materials present in the room distorted the magnetic fields that MRI equipment depended upon for reliable imaging. In extreme cases, the MRI magnet, a key component in the imaging equipment, exerted force on the current-carrying filaments in light bulbs, thereby substantially shortening the light bulbs' lives. Optimally, no ferrous materials should be placed within the 5 Gauss region of operating MRI equipment.

Second, electromagnetic radiation generated by the electron flow through discharge lighting devices (fluorescent lamps, for example) can cause MRI image failures, poor quality MRI readings, and even false MRI readings. Hence, to ensure accurate readings, some lighting systems needed to be completely shut down prior to operating the MRI equipment.

This invention is a lighting system that resolves all of the aforementioned issues. This invention produces a quality white or other color light through the use of high-intensity LED's, which can be used during MRI operation. Essentially, this invention is a direct replacement for existing incandescent and fluorescent lighting systems.

There are problems that arise from the use of high-intensity LED lighting. One problem is that LED performance and life is adversely affected by heat. This heat must be removed from the LED's themselves and effectively conducted to an area where it can be safely dissipated. This problem is further exacerbated by use of standard fiberglass circuit board (such as the circuit board used in U.S. Pat. No. 6,354,714 to Rhodes 2002, which claims a lighting strip for marking walkways and the like), which cannot be efficiently thermally-connected to a heat sink. The result is the plastic LED components can overheat and fail.

Another problem is the hot spots that are created by the intense light of the multiple LED point sources. If not corrected, these hot spots produce excessive glare and an appearance that is not aesthetically pleasing to the user.

BACKGROUND OF THE INVENTION

This invention provides a quality white or other color light that can be used during operation of MRI equipment. This quality white or other color light can be dimmed to provide flexible lighting levels. The flexible lighting levels can range from the maximum light used for patient procedures and equipment servicing/maintenance to the lowest light level used to keep a patient comfortable while facing upward on the MRI scanning table.

Moreover, by using a thermally-conductive substrate printed circuit board, this invention resolves the thermal issues associated with the high-intensity light generated by multiple LED's. The thermally-conductive printed circuit board consists of an aluminum plate that is selectively coated with an electrical insulator (coating remains only where the electrical circuits will be formed) and then forming the electrical circuits using what is known as "fully additive" circuit processes. Thus, the aluminum substrate printed circuit board creates an isolation layer and, then, a conductive layer. These layers isolate the LED's electrically, but not thermally, from the heat sink. The aluminum plate provides a direct thermal connection to the high-intensity LED components.

The lighting level issues are resolved by the incorporation of a reflector around each LED and a diffuser lens located at the light fixture's opening. This combination makes the light softer, as well as more uniform and even. This combination also protects the user and installer from electrical hazards associated with the potentially high voltages within the light fixture itself To date, no one has created such an MRI-compatible lighting system, and no other manufacture offers an LED lighting system for use in conjunction with operating MRI equipment.

BRIEF SUMMARY OF THE INVENTION

This invention is a lighting system consisting of a group of LED lighting fixtures wired to an alternating current (AC) mains power source and optionally interconnected to a proprietary dimmer control circuit.

The LED lighting fixtures consist of five (5) major elements: an LED light source, a beam-forming optical system, a power converter/regulator, a thermal management system, and an enclosure or supporting frame.

The LED light source consists of a thermally-conductive substrate printed circuit board with a plurality of high-intensity LED's attached. The plurality of LED's are connected electrically in series and then are connected to a constant-current source. By doing this, there is no need for "current limiting" or "series" resistors (as are needed in U.S. Pat. No. 6,871,981 to Alexanderson, et al. (2005), which claims an LED lighting system for car interiors). Current limiting series resistors create additional heat, waste electrical energy and occupy valuable space in the area of the LED's.

The beam-forming optical system consists of one or more reflectors and a translucent diffuser or lens. One or more reflectors can be employed either in conjunction with individual LED's, or to enclose a group of LED's. An array of reflectors is molded of a plastic material, such as, polycarbonate, into a single unit and metalized to provide a highly specular reflective surface. Coatings can be applied to the reflector surfaces to provide diffuse light scattering. The polycarbonate material also provides an electrical barrier to the LED circuitry, which may be operating at high voltage. The diffuser mixes the light rays from the individual LED's into a single beam of the desired radiation pattern. The diffuser also mixes any color discrepancies in the individual LED's into a uniform, homogeneous colored beam. The diffuser additionally removes the glare of the individual LED point light sources. Lastly, the diffuser lens provides an additional protection barrier for the user and the installer from the electrical hazards associated with the potentially high voltages within the light fixture itself.

The diffuser can be made of glass, plastic or any material which efficiently transmits light. It can be molded into a refracting lens or series of lenses. It can also be made of a clear substrate material with optical treatments applied to it. One such treatment involves the use of non-imaging microstructure materials that incorporate a multitude of miniature "lenses" engineered to provide a controlled radiation pattern with a high degree of light transmission. The use of a multitude of micro-lenses causes the desired mixing of the individual LED light rays without creating visible images of the point sources or color variations.

A large, single reflector encloses the LED source, reflector array, and diffuser to create a unified "light engine." Generally, this light engine is installed in a ceiling opening and appears to an observer as an ordinary incandescent light fixture.

The power converter/regulator converts mains power (typically 120 to 240 Volts AC) to a regulated DC current that can operate the LED's at a given light level. This AC to DC converter uses switching technology to reduce the heat dissipation and maximize the current source's power efficiency. Switching converters generally have a fundamental frequency associated with their design. For this invention, it is best to select a frequency and wave shape that does not cause MRI-sensitive radio frequency emissions. Additional circuit components are selected to virtually eliminate electromagnetic radiation that would interfere with operating MRI equipment. The circuit topology is designed for easy addition of Power Factor Correction (PFC) for use where required by government regulations.

The thermal management system removes heat from the LED devices and dissipates that heat into the environment. It consists of the aluminum substrate printed circuit board to which the LED's are mounted and a heat sink assembly. The thermally-conductive substrate printed circuit board creates an electrical circuit for interconnecting the LED's and conducts heat away from them much more effectively than a traditional fiberglass substrate printed circuit board. The thermally-conductive substrate printed circuit board is thermally bonded to the heat sink, which is extruded thermally-conductive with sufficient heat radiating and emission area as well as sufficient thermal conductivity to the heat radiating surfaces.

The enclosure or supporting frame mechanically connects the various optical, thermal, and electronic subassemblies and provides a means for mounting the integrated fixture into a ceiling or wall structure. The most common version of the enclosure or supporting frame is called a "down light," but other configurations are possible (wall sconces, indirect lighting, etc.). The down light fixture is typically mounted in a recessed ceiling tile or drywall ceiling. In order to facilitate installation, the down light fixture is designed to be supplied in two (2) major parts: (1) the "basic frame," which includes the supporting elements, power converter/regulator, and electrical junction box; and (2) the "light engine," which consists of the LED array, optical assembly, and thermal management components. The basic frame is installed above the ceiling, and the light engine is inserted from below the ceiling and captured by spring clips in the frame. The basic frame and light engine are then electrically connected by a connector harness.

The end result is that the radiation issues associated with fluorescent, incandescent, or metal halide lighting systems have been eliminated, without the thermal, glare, and hot spot issues associated with high-intensity LED lighting. This combination of elements has never been used to create such a lighting system, and no other manufacturer offers a product such as this.

In one embodiment, the invention provides an electromagnetically shielded light fixture that includes a frame, at least one reflector, a light emitting diode ("LED") light source, a heat sink, and a control circuit. The LED light source includes a non-ferrous printed circuit board ("PCB") and one or more LEDs, and the heat sink is in thermal communication with the LED light source. The control circuit receives power from a power source and provides a regulated operational current to the LED light source. The control circuit includes at least one switch for interrupting the flow of current through the control circuit. The switch has a first state and a second state, and the operational current provided to the LED light source is increased and decreased in a linear manner based on the state of the at least one switch.

In another embodiment, the invention provides an electromagnetically shielded, non-ferrous light fixture that includes a frame, a reflector, an LED light source, and a control circuit. The LED light source includes a PCB and one or more LEDs. The control circuit receives power from an AC power source and provides a regulated operational current to the LED light source. The operational current provided to the LED light source has a triangular wave shape.

In yet another embodiment, the invention provides a non-ferrous light fixture that includes an LED light source and a control circuit. The LED light source includes one or more LEDs, and the control circuit receives power from a power source and provides a regulated operational current to the LED light source. The control circuit includes at least one transistor for controlling the flow of current through the control circuit. The transistor has a first state and a second state, and the operational current provided to the LED light source is increased and decreased in a linear manner based on the state of the at least one transistor.

Other aspects of the invention will become apparent by consideration of the detailed description and accompanying drawings.

DRAWINGS—REFERENCE NUMERALS

200-Basic frame
201-Beam shaping lens

202-Main reflector
203-Support legs (for the diffuser)
204-Reflector array
205-(High-power) LEDs
206-Heat sink
207-Aluminum substrate printed circuit board
208-Power converter/regulator assembly
209-Electrical field wiring junction box

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Lighting System

Figure 1:
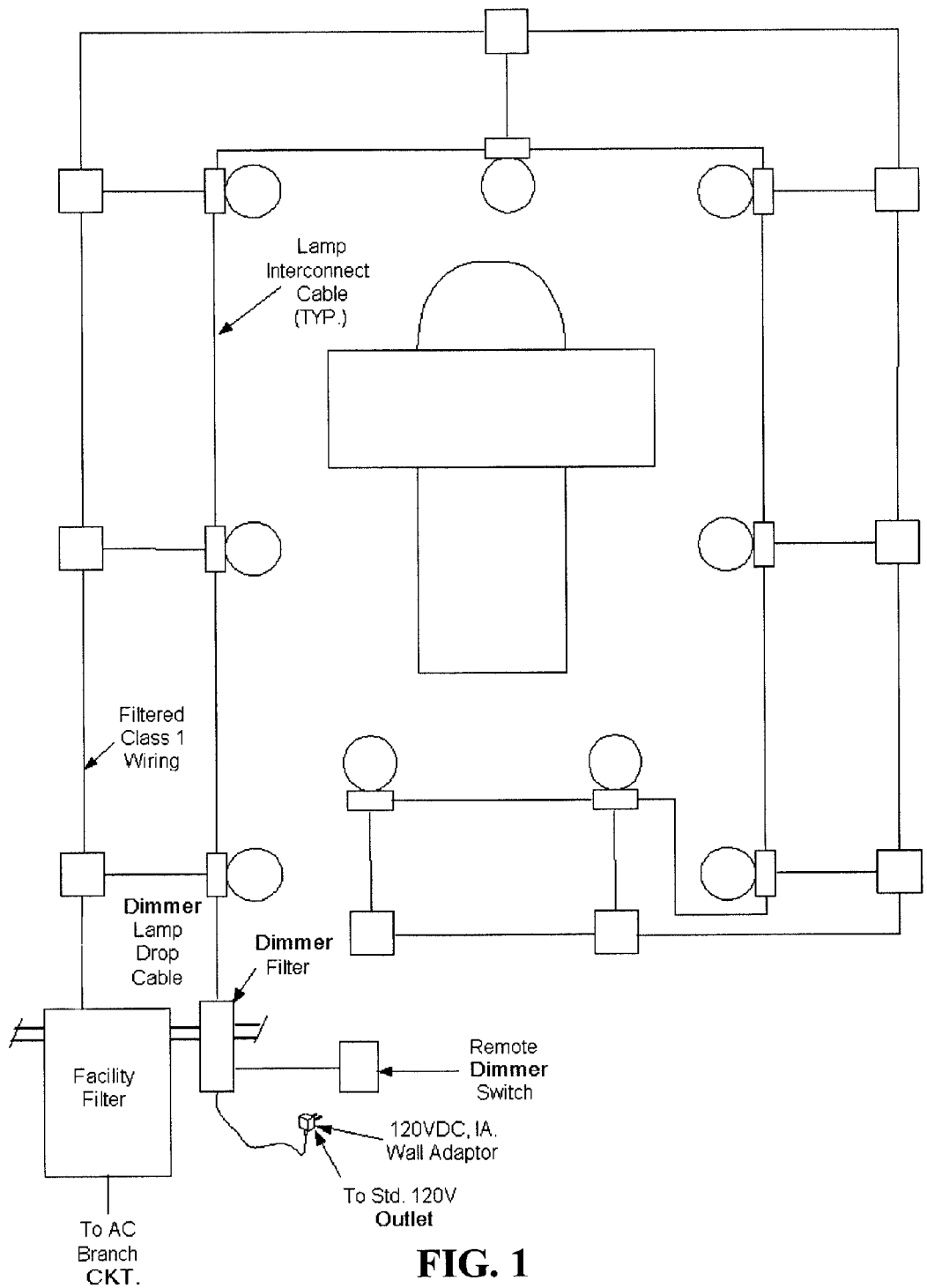
FIG. 1-Block diagram of a typical MRI room.

FIG. 1 is a block diagram of a typical MRI room. The MRI magnet imaging equipment and patient table are centrally located in the room, which is (and must be) enclosed by an electromagnetic shield. This shield must include all doors, windows, vents, and any other penetrations into the room.

The LED lighting fixtures LF1 through LF9 are powered by ordinary mains AC supplied via junction boxes and conduit as specified by applicable electrical codes. Power for the lighting circuit is supplied to the room through an EMI facility filter installed on the outside of the room shield on a penetration panel. This ensures that any EMI signals on the power line are removed or reduced to an acceptable level before entering the room.

The LED lighting fixtures are optionally connected to a dimmer control circuit via low-voltage Class 2 Lamp Interconnect Cables in a "daisy-chain" fashion. The dimmer control circuit also passes through a filter on the penetration panel to remove any EMI from outside the MRI room. The actual dimmer control and power supply are typically located remotely outside the room.

LED Lighting Fixture

Figure 2:
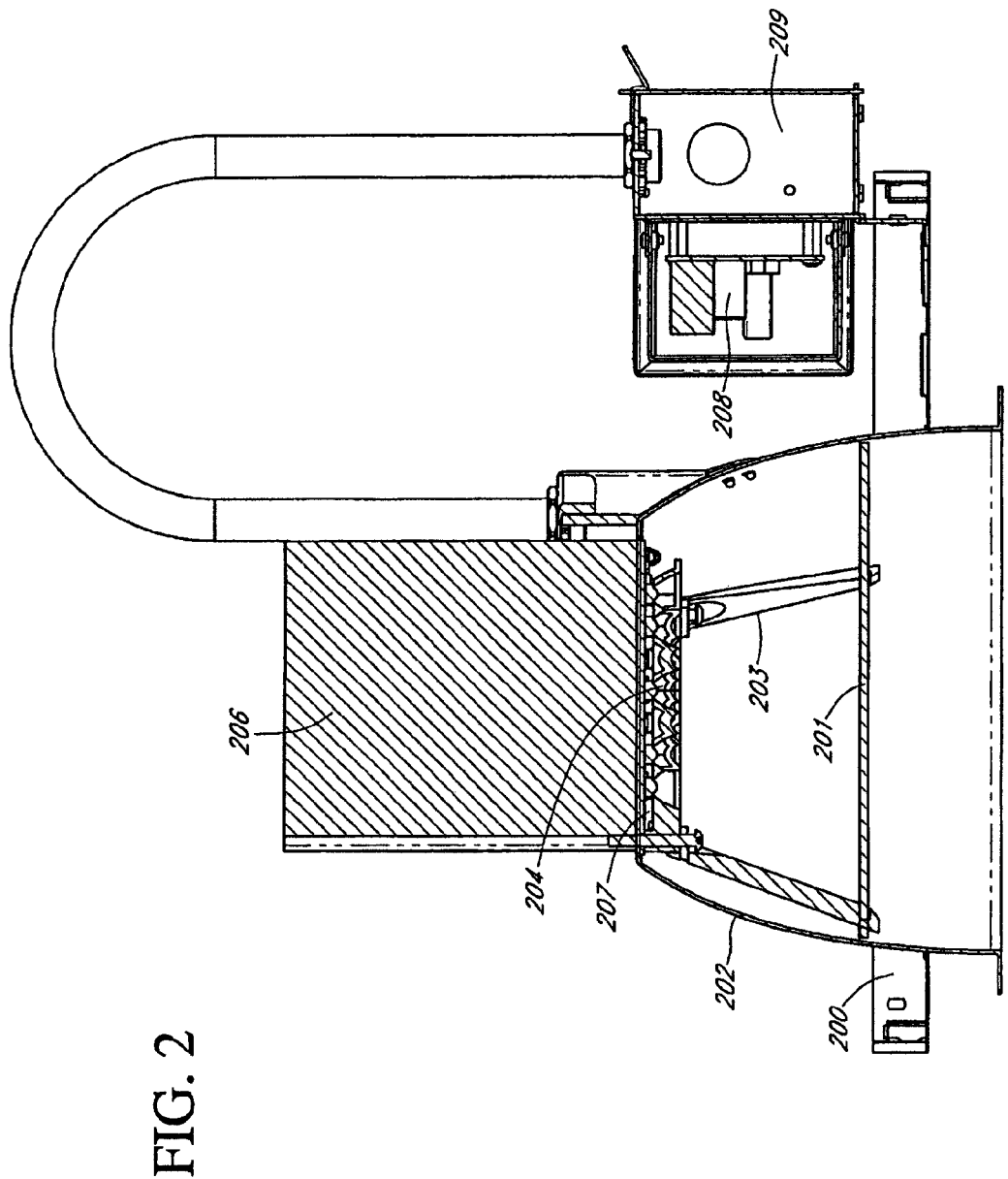
FIG. 2-LED lighting fixture and its components.

FIG. 2 depicts the LED lighting fixture and its components. The basic frame 200 supports the various components, including the power converter/regulator assembly 208, the electrical field wiring junction box 209 and spring clips, which engage the light engine. The light engine consists of the LED array, optical assembly, and thermal management components. The basic frame is installed above the ceiling, and the light engine is inserted from below the ceiling and captured by spring clips in the frame. The basic frame and the light engine are then electrically connected by a shielded wire harness. All of the fixture components are manufactured from non-ferrous materials, such as aluminum, stainless steel, brass, copper, and various types of plastic or glass.

LED Light Source & Thermal Management

Figure 3A:
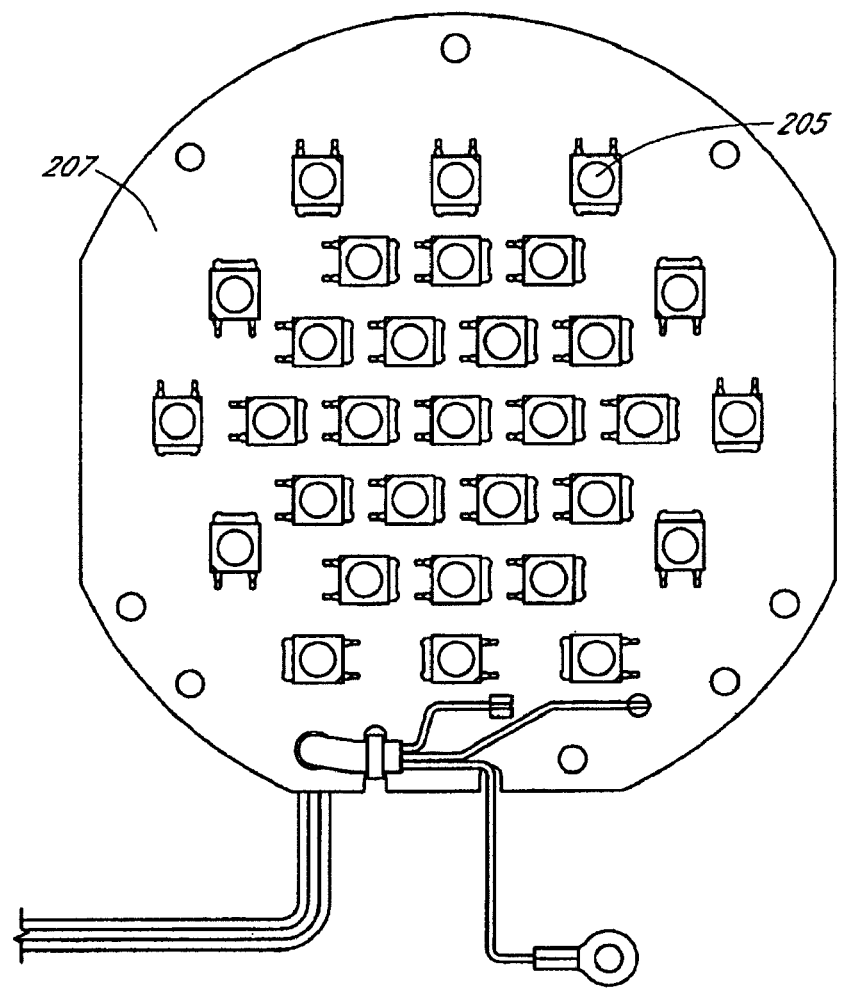
FIG. 3A-Assembly Diagram of the LED Light Source Panel.
Figure 3B:
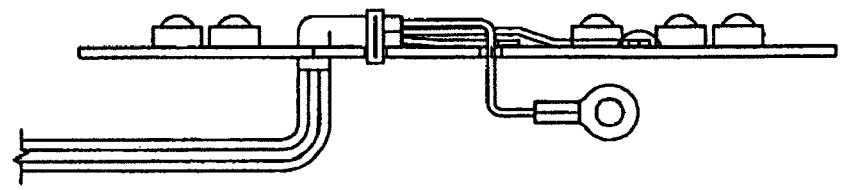
FIG. 3B-Side view of Assembly Diagram of the LED Light Source Panel.

The LED light source is comprised of an aluminum substrate printed circuit board 207 (PCB) with LED's, and the primary heat sink 206. FIG. 3 shows the aluminum PCB containing thirty-one (31) high-power LED's 205 mounted in a symmetrical or nearly symmetrical array. The base material is aluminum with a dielectric coating applied to the surface. On top of this surface are conductive traces that provide a means of creating an electronic circuit board. This combination allows heat from the LED's to conduct through to the main heat sink. The LED's are electrically connected in a series arrangement so that the drive current from the power converter/regulator passes through each LED, and each LED "sees" the same electrical current. Optionally, the LED circuit may contain a thermal cutout device, protecting the LED's and fixture from overheating.

Optics

Figure 4:
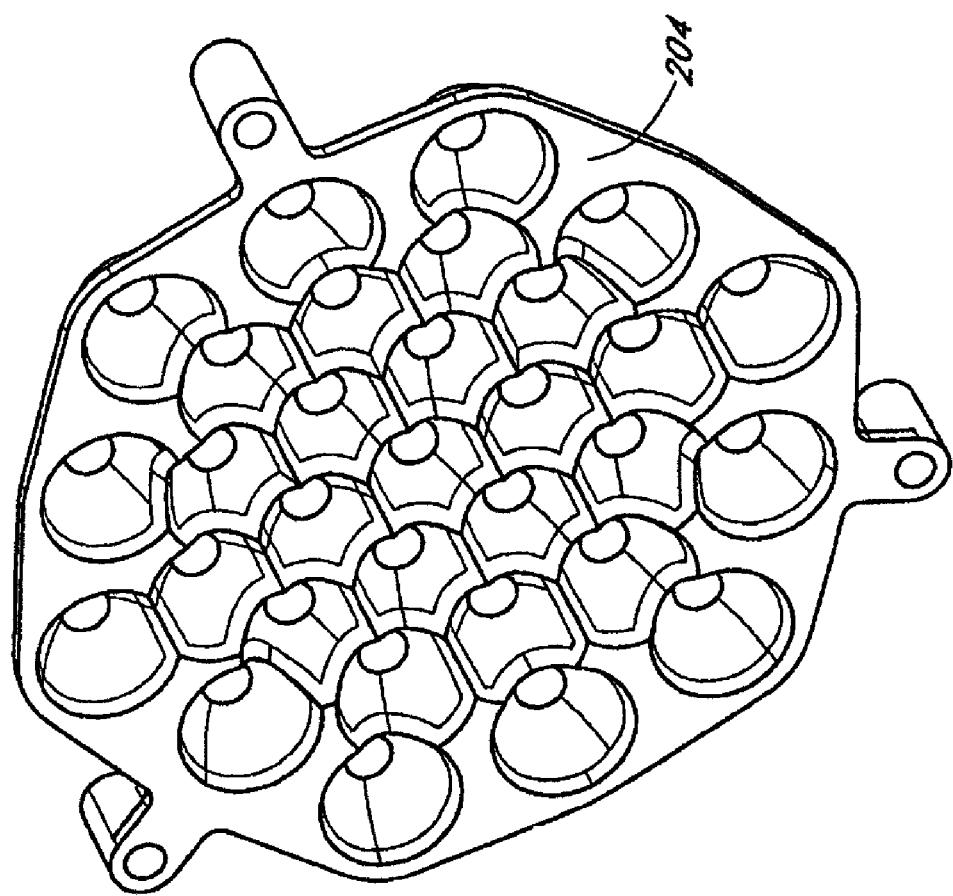
FIG. 4-Reflector Array.
Figure 5A:
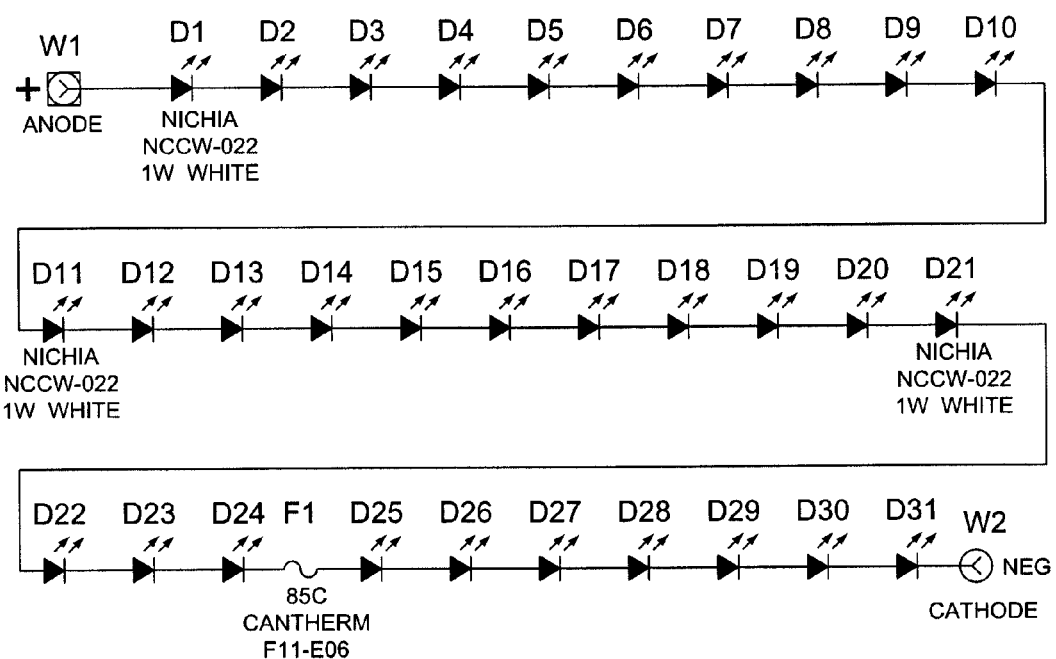
FIG. 5A-Schematic diagram of the LED PC Board.
Figure 5B:
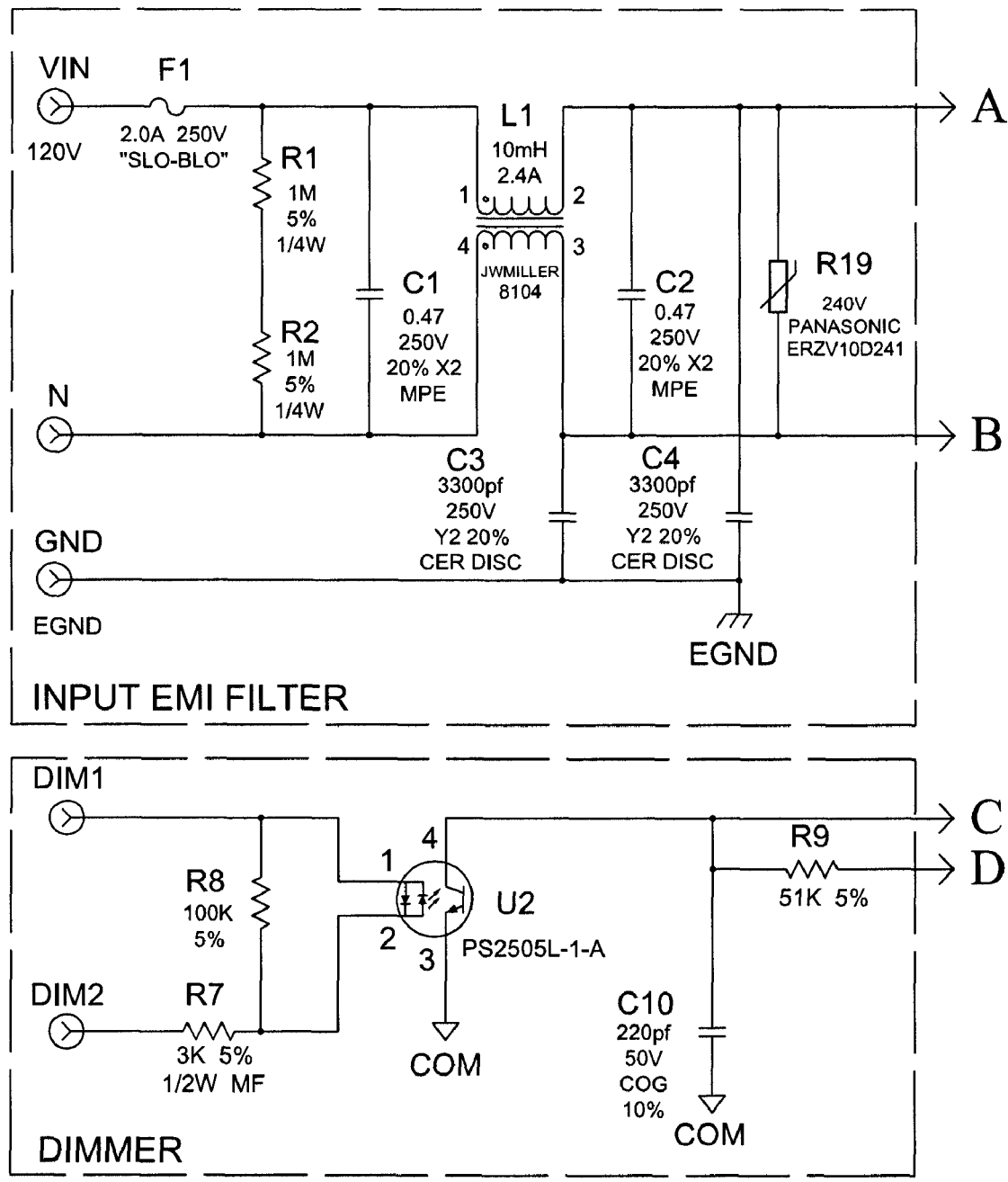
FIGS. 5B-5D - Schematic diagram of the Current Source Driver.
Figure 5C:
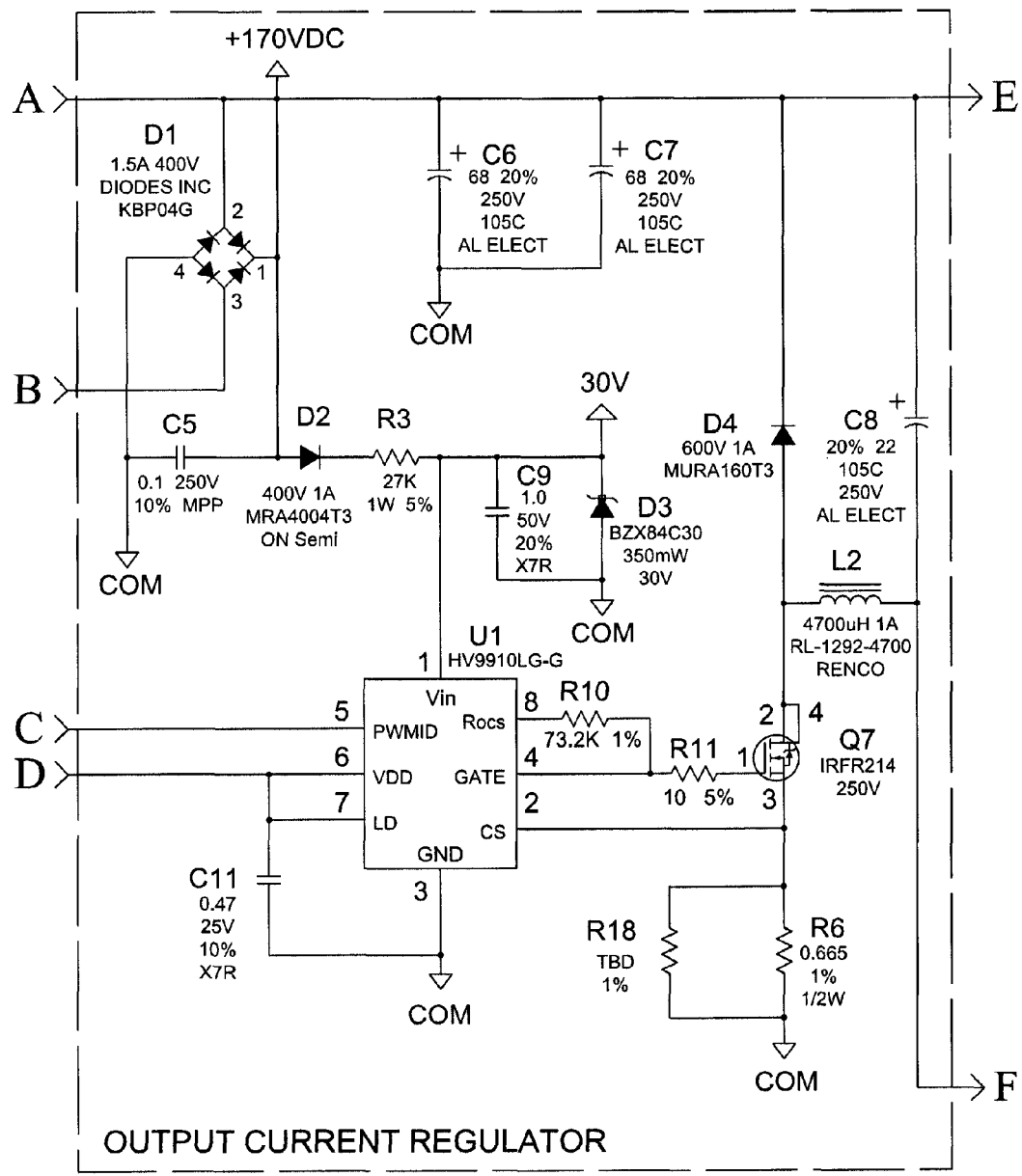
Figure 5D:
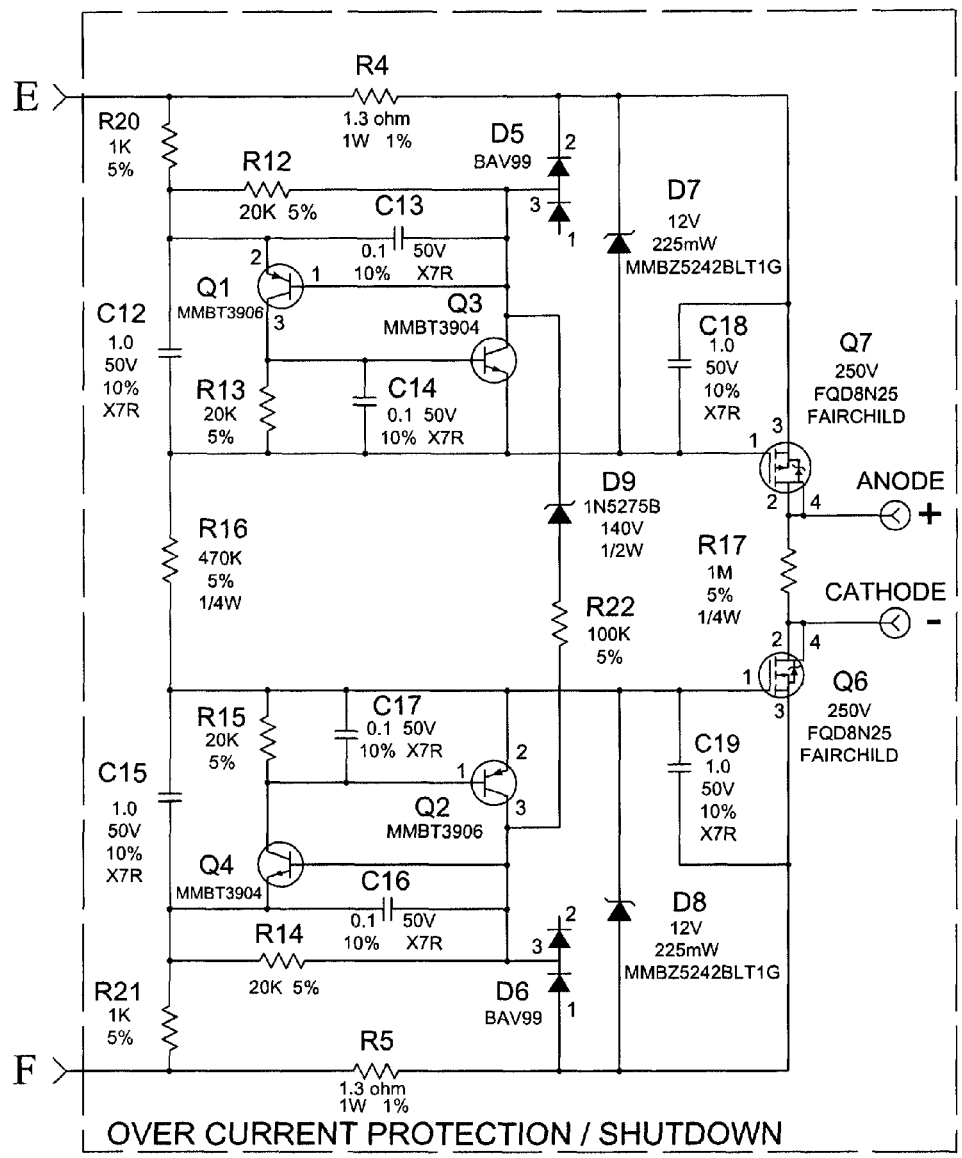

The cross section of FIG. 2 shows the three (3) major optics components: a reflector array 204 or series of individual reflectors, a beam-shaping lens 201 or diffuser, and a main reflector 202. The reflector array is comprised of either a series of parabolas, or individual parabolas, each with its focal point located at the point of radiation of its respective LED's 205. The parabolas have a specular (or diffuse) reflective coating so as to collimate the light emitted by their respective LED's. Additionally, the base material of the reflectors is such that it provides a dielectric barrier between the outside world and the aluminum PCB. FIG. 4 illustrates the reflector array.

The beam-shaping lens is comprised of a plate of optical grade material with a series of optical elements designed to provide a specific spread or beam pattern. It may be glass, plastic, or other suitable optical grade material. The optical elements may vary micro-structures to 4-5 mm across. The distance from the beam-shaping lens to the LED's is set by a mounting structure so as to maintain a constant distance from the LED's.

The main reflector is an aluminum parabola with a specular (or diffuse) finish and the aluminum substrate PCB mounted at or near its focal point. This reflector serves to gather light not managed by the reflector array and redirect it in the desired direction (towards the beam-shaping lens). This reflector serves as a mounting structure for the aluminum substrate PCB/heat sink assembly, acts as a secondary heat sink for the system, and provides an electrical enclosure for the LED circuitry.

Various combinations of these components can be used, depending on the desired illumination characteristics and system cost. The minimal configuration would consist of the LED array and overall reflector only. In order to reduce glare and spread the illumination pattern, the diffuser is added. For a more focused beam, the reflector array is employed, with or without the diffuser.

In the preferred embodiment, the LED array is matched to a metalized reflector array to effectively collimate the beam into a diffuser constructed of micro-lenses. The main overall reflector encloses the entire optics assembly and provides the mechanical structure that engages the frame's spring clips and to which the LED and heat sink assemblies are attached.

Power Converter/Regulator

The power converter/regulator is comprised of four (4) major functional sections: Input EMI Filter; Output Current Regulator; Dimming Control; and Over Current Protection/Shutdown. These are shown on FIG. 5.

The Input EMI Filter section, comprised of suppression capacitors C1, C2, C3, and C4, and Common Mode choke L1, provides sufficient attenuation of radio frequency signals detrimental to the MRI environment that may be conducted out through the mains power wiring. Additional components, known as feed-through capacitors, provide the required attenuation of radiated radio frequency signals. Resistors R1 and R2, and varistor R19 provide the safety functions of input capacitive discharge and mains surge protection respectively.

The Output Current Regulator section serves two (2) major functions: to convert the mains AC current into a DC current, and to control the DC output voltage so that a constant current is applied to the load. Bridge rectifier D1 and bulk capacitors C6 and C7 convert the mains AC to a relatively constant voltage of approximately Vin(RMS)×√2. For a typical 120V utility, this voltage is approximately 170V. Capacitor C5 provides a very low impedance current reservoir for high-frequency switching purposes. Diodes D2 and D3, R3 and C9 tap off this 170V bus to provide a low-current bias supply for the control circuitry at about 30V. Connections for additional Power Factor Correction circuitry are easily provided by removing jumpers and installing an optional module.

To understand the operation of the current regulation circuitry, it is helpful to imagine a load impedance in parallel with output capacitor C8, and to ignore the protection circuitry that exists beyond that point. The integrated circuit control chip, U1, provides output current regulation by switching a power transistor, Q7, OFF for a fixed period of time and then ON for variable period in response to a feedback signal generated across sense resistors R6 and R18. When the transistor is turned ON, current flows from the 170V bus, through the load, through inductor L2, through Q7, and finally through R6 and R18. The inductor limits the current's rate of increase linearly until the level reaches the control chip's internal set point determined by the value chosen for R6 and R18. At this point, the transistor is commanded to turn OFF. In response to this, L2 attempts to maintain the existing current flow by reversing polarity, forward biasing diode D4, and continuing to power the load. The fixed OFF time is chosen to allow the inductor current to drop to a set constant value before the next ON cycle begins. The resulting wave-shape is a triangle with average DC levels that equal the desired load current. Any change in input voltage or output load is compensated for by a proportional change in the ON time caused by the feedback signal across the sense resistors. This triangular wave-shape is important to the use of this circuit in low EMI environments, such as rooms with operating MRI equipment. The triangular wave-shape does not contain the multitude of harmonic frequencies that make up the square wave-shapes typically employed in switch mode regulators.

Dimming Control is provided by optical coupler U2, resistors R7, R8, and R9, and capacitor C10. Because the dimming system uses Class 2 wiring for ease of installation, it must be galvanically isolated from the current regulator circuitry, which itself operates at mains potential. The optical coupler performs the isolation function and eliminates potential wiring errors by allowing non-polarized signal connections. Resistors R7 and R8 create a voltage divider that adds some level of noise immunity and guarantees that the opto-coupler will be OFF if no signal is applied. The output side of the opto-coupler enables or disables the current control chip, thereby creating a "pulse group modulation" whereby either full current, or no current is applied to the load at a rate that is fast enough to be undetectable to the naked eye. Modulation applied in this fashion results in very linear apparent dimming without affecting the color temperature of the LED's. Resistor R9 and capacitor C10 provide additional noise filtering and a "pull-up" function that keeps the control chip active if the opto-coupler is deactivated.

Finally, the Over Current Protection/Shutdown provides a measure of safety in the event of a component failure or external wiring short circuit. There are actually two (2) distinct and separate circuits involved that are mirror images of each other. One monitors the positive load output terminal, while the other monitors the negative terminal. Field Effect Transistor (FET) Q5 (Q6) and sense resistor R4 (R5) are connected in series with the current regulator output node and the load. The transistor is sized to handle 2× the continuous load current and is initially held in the ON state by current flow through R16 and D8 (D7). At normal output current levels, the voltage drop across the sense resistor is insufficient to forward-bias sense transistor Q1 (Q4). However, when the output current reaches a fault level, current flows through R20 (R21), Q1 (Q4), and D5 (D6). As Q1 (Q4) turns ON, current flows through Q3 (Q2) creating positive feedback which causes the circuit to latch ON. This action in turn brings the gate of Q5 (Q6) to within 1.5V of its source thereby causing Q5 (Q6) to turn OFF. The total response time is fast enough to protect a semiconductor load from excessive power dissipation, even with several amperes of peak current applied. D5 (D6) allows the latch to continue to operate once the load is removed by isolating the base of Q1 (Q4) from the output node. Resistors R12 (R14) and R20 (R21), and capacitor C13 (16) set the trip response time, which can mimic any typical fuse response from "fast" to "slow blow," while R13 (R15) and C14 (C17) provide an initial turn-on delay to avoid transient nuisance tripping. Clamp diodes D7 and D8 protect the FET gates from excess voltages. Lastly, D9 and R22 provide a current path between the two (2) shutdown circuits that causes one or both latches to activate if the output terminal voltage rises above mandated safety levels, i.e. over-voltage protection.

The power converter/regulator and dimmer circuits are enclosed in a non-ferrous Faraday shield to prevent radiated emissions, which would interfere with the MRI scanner signals. To prevent conducted emissions on the power input, LED output, and dimmer control leads, feed-through capacitors FC1 through FC6 are employed at the points these conductors enter/exit the shield enclosure.

What is claimed is:

1. An electromagnetically shielded light fixture comprising:
    a frame;
    at least one reflector;
    a light emitting diode ("LED") light source including a printed circuit board ("PCB") and one or more LEDs;
    a heat sink in thermal communication with the LED light source; and
    a control circuit configured to receive power from a power source and to provide a regulated operational current to the LED light source,
    wherein the control circuit includes an inductor and at least one switch configured to interrupt the flow of current through the control circuit, the switch having a first state and a second state, and
    wherein the inductor and the switch cooperate to provide a triangle wave operational current to the LED light source, wherein the current is increased and decreased in a linear manner based on the state of the at least one switch and the polarity of the inductor.

2. The light fixture of claim 1, wherein the light fixture is completely non-ferrous.

3. The light fixture of claim 2, wherein the light fixture is at least partially constructed of at least one of the following materials: aluminum, stainless steel, glass, brass, copper, and plastic.

4. The light fixture of claim 1, wherein the light fixture is configured to be powered by AC mains power.

5. The light fixture of claim 1, wherein the fixture is configured to output a homogenous colored beam.

6. The light fixture of claim 1, wherein the light fixture includes a down light fixture.

7. The light fixture of claim 1, further comprising a dimmer configured to provide linear dimming of the light fixture.

8. An electromagnetically shielded light fixture for use in a shielded room, the fixture comprising:
    a frame;
    a reflector;

a light emitting diode ("LED") light source positioned within the shielded room and including a printed circuit board ("PCB") and one or more LEDs; and a control circuit positioned outside of the shielded room and configured to receive power from an alternating current ("AC") power source and to provide a regulated operational current to the LED light source, wherein the operational current provided to the LED light source has a triangular wave shape.

9. The light fixture of claim 8, further comprising a heat sink in thermal communication with the LED light source.

10. The light fixture of claim 8, wherein the light fixture is at least partially constructed of at least one of the following materials: aluminum, stainless steel, glass, brass, copper, and plastic.

11. The light fixture of claim 8, wherein the light fixture is configured to be powered by AC mains power.

12. The light fixture of claim 8, wherein the fixture is configured to output a homogenous colored beam.

13. The light fixture of claim 8, wherein the light fixture is a down light fixture.

14. The light fixture of claim 8, further comprising a dimmer configured to provide linear dimming of the light fixture.

15. A light fixture for use in an electromagnetically shielded room, the fixture comprising:

a light emitting diode ("LED") light source positioned within the shielded room and including one or more LEDs; and a control circuit positioned outside of the shielded room and configured to receive power from a power source and to provide a regulated operational current to the LED light source, wherein the control circuit includes at least one transistor configured to interrupt the flow of current through the control circuit, the transistor having a first state and a second state, wherein the control circuit includes an inductor operable in a first polarity to limit the rate of operational current increase and operable in a second polarity to limit the rate of operational current decrease, wherein the operational current provided to the LED light source is increased and decreased in a linear manner based on the state of the at least one transistor and the polarity of the inductor, and wherein the light fixture is non-ferrous.

16. The light fixture of claim 15, wherein the light fixture is at least partially constructed of at least one of the following materials: aluminum, stainless steel, glass, brass, copper, and plastic.

17. The light fixture of claim 15, wherein the light fixture is configured to be powered by AC mains power.

18. The light fixture of claim 15, wherein the light fixture is a down light fixture.

19. The light fixture of claim 15, further comprising a dimmer configured to provide linear dimming of the light fixture.

20. The light fixture of claim 15, wherein the fixture is configured to output a homogenous colored beam.

* * * * *